(12) United States Patent
Yocum

(10) Patent No.: US 10,466,221 B2
(45) Date of Patent: Nov. 5, 2019

(54) SYSTEMS AND METHODS FOR PREDICTING GAS CONCENTRATION VALUES

(71) Applicant: Industrial Scientific Corporation, Pittsburgh, PA (US)

(72) Inventor: Christopher Todd Yocum, Gibsonia, PA (US)

(73) Assignee: Industrial Scientific Corporation, Pittsburgh, PA (US)

(*) Notice: Subject to any disclaimer, the term of this patent is extended or adjusted under 35 U.S.C. 154(b) by 115 days.

(21) Appl. No.: 15/106,452

(22) PCT Filed: Dec. 22, 2014

(86) PCT No.: PCT/US2014/071968
§ 371 (c)(1),
(2) Date: Jun. 20, 2016

(87) PCT Pub. No.: WO2015/095884
PCT Pub. Date: Jun. 25, 2015

(65) Prior Publication Data
US 2016/0356752 A1    Dec. 8, 2016

Related U.S. Application Data

(60) Provisional application No. 61/918,845, filed on Dec. 20, 2013.

(51) Int. Cl.
*G01N 33/00* (2006.01)

(52) U.S. Cl.
CPC ..... *G01N 33/0067* (2013.01); *G01N 33/0004* (2013.01); *G01N 33/004* (2013.01);
(Continued)

(58) Field of Classification Search
CPC .................................................. G01N 33/0067
See application file for complete search history.

(56) References Cited

U.S. PATENT DOCUMENTS 4,074,243 A * 2/1978 Bogen ............... G01N 33/0067
340/501
5,418,131 A * 5/1995 Butts ..................... C12M 41/14
236/2

(Continued)

OTHER PUBLICATIONS

PCT/US2014/071968, "International Application Serial No. PCT/US2014/071968, International Preliminary Report on Patentability and Written Opinion dated Jun. 30, 2016", Industrial Scientific Corporation, 7 Pages.

*Primary Examiner* — Hyun D Park
(74) *Attorney, Agent, or Firm* — GTC Law Group PC & Affiliates (57) ABSTRACT

Methods and systems for predicting gas concentration values are described, which may include predictions based on gas measurement information received from a gas sensor and gas sensor response information for the gas sensor. The gas sensor response information which may be in the form of a sigmoid function. In some embodiments, the predicted gas concentration values may be generated by predicting an asymptotic value of the gas measurement information based on a rate of change of the concentration of the gas and the gas sensor response information.

14 Claims, 7 Drawing Sheets

(52) U.S. Cl.
CPC ..... *G01N 33/0037* (2013.01); *G01N 33/0042* (2013.01); *G01N 33/0044* (2013.01); *G01N 33/0063* (2013.01); *Y02A 50/245* (2018.01)

(56) References Cited

U.S. PATENT DOCUMENTS

| | | | | |
|---|---|---|---|---|
| 6,107,631 | A * | 8/2000 | He | G01N 21/274 |
| | | | | 250/339.01 |
| 2002/0092525 | A1* | 7/2002 | Rump | A62B 9/006 |
| | | | | 128/205.23 |
| 2003/0233212 | A1* | 12/2003 | Von Drasek | C21C 5/40 |
| | | | | 702/179 |
| 2004/0249578 | A1* | 12/2004 | Ammouri | G01N 33/0031 |
| | | | | 702/24 |
| 2016/0334378 | A1 | 11/2016 | Maddila et al. | |

* cited by examiner

SYSTEMS AND METHODS FOR PREDICTING GAS CONCENTRATION VALUES

CROSS REFERENCE TO RELATED APPLICATIONS

This application claims the benefit of U.S. Provisional Application No. 61/918,845 filed on Dec. 20, 2013, the contents of which are incorporated by reference in their entirety as if fully set forth herein.

BACKGROUND

Gas monitoring systems are used in industrial facilities to protect people and property from various environmental conditions, such as toxic gas exposure, oxygen asphyxiation, and risk of explosion. In general, gas monitoring systems operate to alleviate such risks by detecting concentrations of certain gases and providing alerts for dangerous conditions in sufficient time to allow individuals to take precautions. Conventional gas detection may be performed using various techniques, including via "fixed" monitors mounted to permanent structures or by "portable" monitors worn or carried by an individual.

The performance of gas monitoring devices may be measured based on the accuracy (or reliability) and the speed of the device. Accuracy is a measure that generally indicates how similar a gas concentration detected by a device is to the actual concentration of the gas in the environment. The speed of a device relates to the time required for the device to react to a change in concentration of a target gas. In a conventional gas monitoring device, speed may be measured in terms of the time required to detect a given percentage of the actual gas concentration. Standard benchmark measurements for speed include "T50" and "T90," which refer to the time required for a gas monitoring device to measure 50% and 90%, respectively, of the actual gas concentration.

Speed is a significant characteristic of any gas monitoring device because affected personnel need to become aware as soon as possible to changing environmental conditions. Improvements in the response times of conventional gas detection hardware, such as sensors and device circuitry, are limited without markedly increasing the cost and/or size of the devices. As such, increasing the speed of a device via hardware is not a realistic option for most gas monitoring device users. Accordingly, gas monitoring devices would benefit from technology that improved the speed of the device through enhancements to techniques for processing gas sensor information to produce a gas measurement output.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a gas monitoring system may include a gas sensor, a processor, and a non-transitory, computer-readable storage medium in operable communication with the processor. The computer-readable storage medium may contain one or more programming instructions that, when executed, cause the processor to receive gas measurement information from the gas sensor for a concentration of a gas, store the gas measurement information as historical gas measurement information, receive gas sensor response information for the gas sensor, determine a rate of change of the concentration of the gas based on the gas measurement information, and generate a predicted gas measurement value for the at least one gas sensor by predicting an asymptotic value of the gas measurement information based on the rate of change and the gas sensor response information.

In an embodiment, a computer-implemented method for monitoring a gas may include, by a processor, receiving gas measurement information from a gas sensor for a concentration of a gas, storing the gas measurement information as historical gas measurement information, receiving gas sensor response information for the gas sensor, determining a rate of change of the concentration of the gas based on the gas measurement information, and generating a predicted gas measurement value for the at least one gas sensor by predicting an asymptotic value of the gas measurement information based on the rate of change and the gas sensor response information.

In an embodiment, a computer-readable storage medium having computer-readable program code configured to monitor a gas may include computer-readable program code configured to receive gas measurement information from a gas sensor for a concentration of a gas, computer-readable program code configured to store the gas measurement information as historical gas measurement information, computer-readable program code configured to receive gas sensor response information for the gas sensor, computer-readable program code configured to determine a rate of change of the concentration of the gas based on the gas measurement information, and computer-readable program code configured to generate a predicted gas measurement value for the at least one gas sensor by predicting an asymptotic value of the gas measurement information based on the rate of change and the gas sensor response information.

BRIEF DESCRIPTION OF THE DRAWINGS

The above and other objects of the present invention will become more readily apparent from the following detailed description taken in connection with the accompanying drawings.

DETAILED DESCRIPTION

The described technology generally relates to systems and methods for detecting environmental gas concentrations. In some embodiments, a gas monitoring device ("gas monitoring system" or "gas detection device") may include various sensors for detecting one or more gases and hardware components for processing and presenting gas detection information obtained by the sensors. Non-limiting examples of hardware components may include a display, processing circuitry (or a "processing unit"), and an alarm. In some embodiments, the processing unit may be configured to receive gas measurement information from a gas sensor relating to the concentration of a gas. In some embodiments, the processing unit may be configured to access gas sensor response information (a gas sensor "profile") relating to gas sensor response characteristics of the gas sensor. The gas sensor response information may be based on various information sources, including, without limitation, historical gas measurement information and/or gas sensor profile information. In some embodiments, the gas monitoring device may be configured to generate a predicted gas measurement value for a gas sensor based on the gas measurement information and/or the gas sensor response information. In some embodiments, generating the predicted gas measurement value may include predicting an asymptotic value of the gas measurement information (for example, using a gas sensor response curve) based on a rate of change of the gas measurement information and the gas sensor response information. In some embodiments, the processing unit may be configured to determine when changes in the gas measurement information (for instance, when a gas sensor is "responding" to a gas) are due to actual changes in gas concentrations and not due to artificial factors, such as temperature, electrical interference, or noise.

Although speed may generally be considered a significant quality characteristic for gas monitoring systems, the competitiveness of this feature in conventional systems has been reduced or even eliminated due to incremental improvements in sensor technology that have essentially leveled the playing field in this regard. In addition, conventional gas monitoring devices are typically microprocessor-based devices that monitor the raw sensor output and provide automated processes for calibration, scaling, noise reduction, and other like signal processing methods. For instance, noise reduction may typically be accomplished by averaging the output of a sensor over a period of time. In an example, if the last three readings from a sensor were 1 parts per million (ppm), 2 ppm, and 3 ppm, the processing unit may provide a gas reading equal to the sum of the readings divided by the number of readings: (1+2+3)/3=2 ppm. Although such noise reduction calculations may provide a stable output, the processing reduces the speed of the device. In another instance, the last three readings of a gas sensor may be 1 ppm, 2 ppm, and 3 ppm. As such, the processing unit would provide an output of 2 ppm. However, in this instance, the increasing reading may be a result of an increasing gas concentration being detected by the sensor. Accordingly, processing circuitry may be configured to reduce or eliminate such noise reduction processing if the processing circuitry determines that the change in the sensor output is due to an actual change in the concentration of a gas (a "gas event") instead of noise. In certain instances, the processing circuitry may present the same value as the raw sensor data to the user.

Even in a scenario in which the processing circuitry causes the raw sensor data to be presented to the user, the speed of the gas monitoring device cannot be faster than the sensor providing the raw data. Accordingly, some embodiments provide for systems and methods for improving gas monitor response times that do not rely on improved gas sensor response times; rather, some embodiments process the sensor output to generate a predicted gas measurement value that may be presented to a user more quickly than a final determination of gas concentration based on the raw data. In some embodiments, a gas monitoring system (or "system") may be configured to determine when a sensor is responding to a gas event and to predict a final asymptotic value of the response curve of the gas sensor, which may be provided as a gas measurement output to a user of the device. In some embodiments, the prediction of the final asymptotic value may be based at least partially on, among other things, a rate of change of the concentration of the gas, the gas sensor response information, the gas measurement information, or any combination thereof.

The gas monitoring systems and methods described according to some embodiments provide multiple technological advantages and technical effects on processes and techniques, including processes and techniques external to the design system. A non-limiting technological advantage generally involves an increase in the speed (or "response time") of a gas monitoring system configured according to some embodiments to provide an accurate reading of a gas concentration to a user when compared with conventional systems. According to some embodiments, the gas monitoring systems and methods improve the gas monitoring process by, for instance, increasing the response time of a gas monitoring system and providing faster readings to gas monitoring system users.

Figure 1:
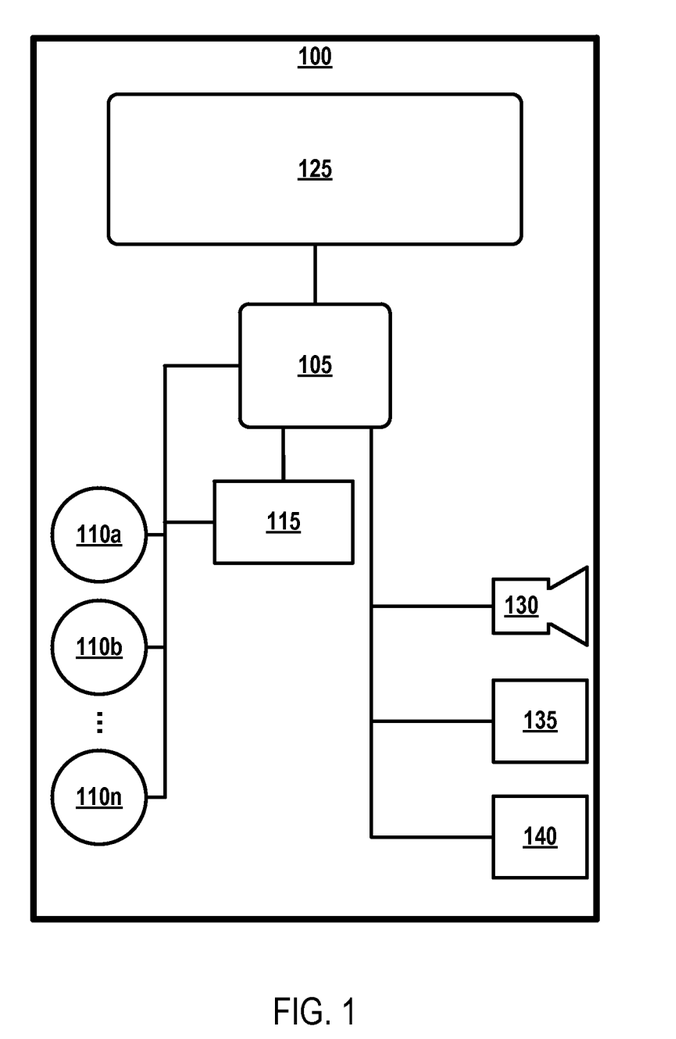
FIG. 1 depicts an illustrative gas monitoring system according to some embodiments.
Figure 7:
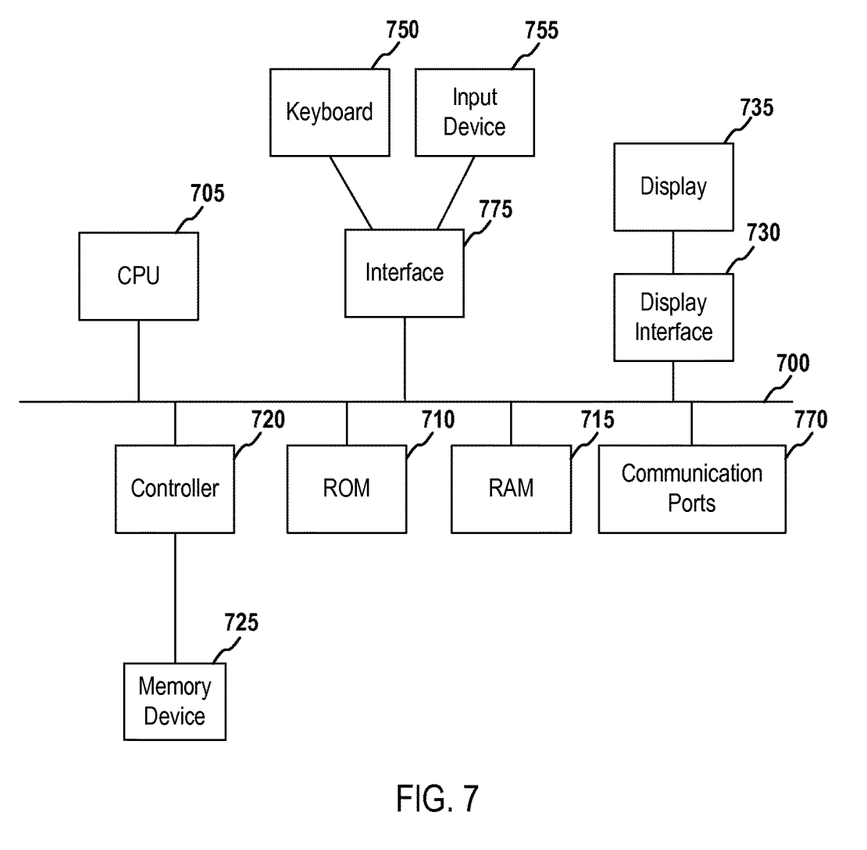
FIG. 7 depicts a block diagram of exemplary internal hardware that may be used to contain or implement the various methods and systems configured according to some embodiments.

FIG. 1 depicts an illustrative gas monitoring system according to some embodiments. As shown in FIG. 1, a gas monitoring system 100 may include a processing unit 105 operably coupled to gas sensors 110a-n. The processing unit 105 may generally include any type of controller, processor, and/or processing circuitry now known to those having ordinary skill in the art or developed in the future, including, without limitation, a CPU 705 and/or a controller 720, as depicted in FIG. 7. The gas sensors 110a-n may be configured to detect the concentration and/or presence of various gases, including, but not limited to, carbon monoxide (CO), oxygen ($O_2$), hydrogen sulfide ($H_2S$), nitrogen dioxide ($NO_2$), and/or sulfur dioxide ($SO_2$). The gas sensors 110a-n may include any type of gas sensor capable of operating in a system 100 configured according to some embodiments. Non-limiting examples of gas sensors 110a-n may include semiconductor sensors (for example, n-type and/or p-type semiconductor sensors), oxidation sensors, catalytic sensors (for example, catalytic bead sensors), photo ionization sensors, infrared sensors, electrochemical sensors, or the like. In some embodiments, the gas sensors 110a-n may include multiple sensors for detecting and/or measuring the same gas. In some embodiments, the gas sensors 110a-n may be positioned in more than one plane or surface of the system 100.

The processing unit 105 may be operably coupled to a data storage element 115, including, without limitation, a storage disc device and/or memory device, such as the ROM 710, RAM 715, and/or memory device 725 depicted in FIG. 7. In some embodiments, the data storage element 115 may be configured to store one or more software applications, instructions, modules, code, or other component capable of being executed by the processing unit 105. In some embodiments, the data storage element 115 may be configured to store information that may be accessed by the processing unit 105, such as gas sensor response information and/or historical gas measurement information. In some embodiments, the data storage element 115 may be operably coupled to one or more of the gas sensors 110a-n and may receive gas measurement information directly from the gas sensors. Although the data storage element 115 is depicted as being internal to the system 100, embodiments are not so limited. For instance, the data storage element 115 may include external storage devices and/or network storage devices.

The processing unit 105 may be configured to receive gas measurement information from the gas sensors 110a-n ("raw gas measurement information") and/or the data storage element 115. The raw gas measurement information may generally include any type of information capable of indicating the presence and/or concentration of a gas. In some embodiments, the processing unit 105 may be configured to process the raw gas measurement information to determine gas concentration information, for instance, through a control application stored on the data storage element 115 and executed by the processing unit. For example, the gas measurement information may include voltage or current information and the processing unit 105 may be configured to calculate a gas concentration value (for instance, parts per million (ppm), parts per billion (ppb), or the like) based on the voltage information.

In some embodiments, the system 100 may include an alarm 130 configured to indicate an unsafe condition or other situation requiring user attention. For instance, the system 100 may be configured to trigger the alarm 130 responsive to a detected gas concentration being outside of a threshold range, the presence of a gas, and/or the absence of a gas (for instance, oxygen). In another instance, the system 100 may be configured to trigger the alarm 130 responsive to events not related to the detection of a gas, such as events relating to power, communication, processing unit operation (for example, software or processing errors), or the like. The alarm 130 may be configured to provide notice of an alarm condition using various methods, such as audio, visual, vibratory, or any combination thereof.

In some embodiments, the system 100 may include a display 125 configured to present information to a user, such as gas measurement information, alarm state, device state, or the like. An input device 135 may be included to allow a user to provide input into the system. The input device 135 may generally include any type of input device capable of providing user input, such as buttons, a keyboard, a mouse, a touch screen, or the like. The system 100 may include a communication port 140 for communicating with other devices and/or a network, including the Internet. The communication port 140 may include, without limitation, a wireless transceiver (for instance, Wi-Fi), an Ethernet port, a telecommunications port (for instance, third Generation (3G), fourth Generation (4G), long-term evolution (LTE), or the like), a Bluetooth interface, a near field communication (NFC) interface, a serial communication port, or the like. In some embodiments, the system 100 may communicate with computing devices and/or networks to obtain information and/or for processing purposes. For instance, the system 100 may be configured to receive gas sensor response information and/or historical gas measurement information from an external information source. In another instance, the system 100 may be configured to transmit information to an external computing device configured to process the information (for example, gas concentration determinations, predicted gas concentration calculations, or the like).

Figure 2:
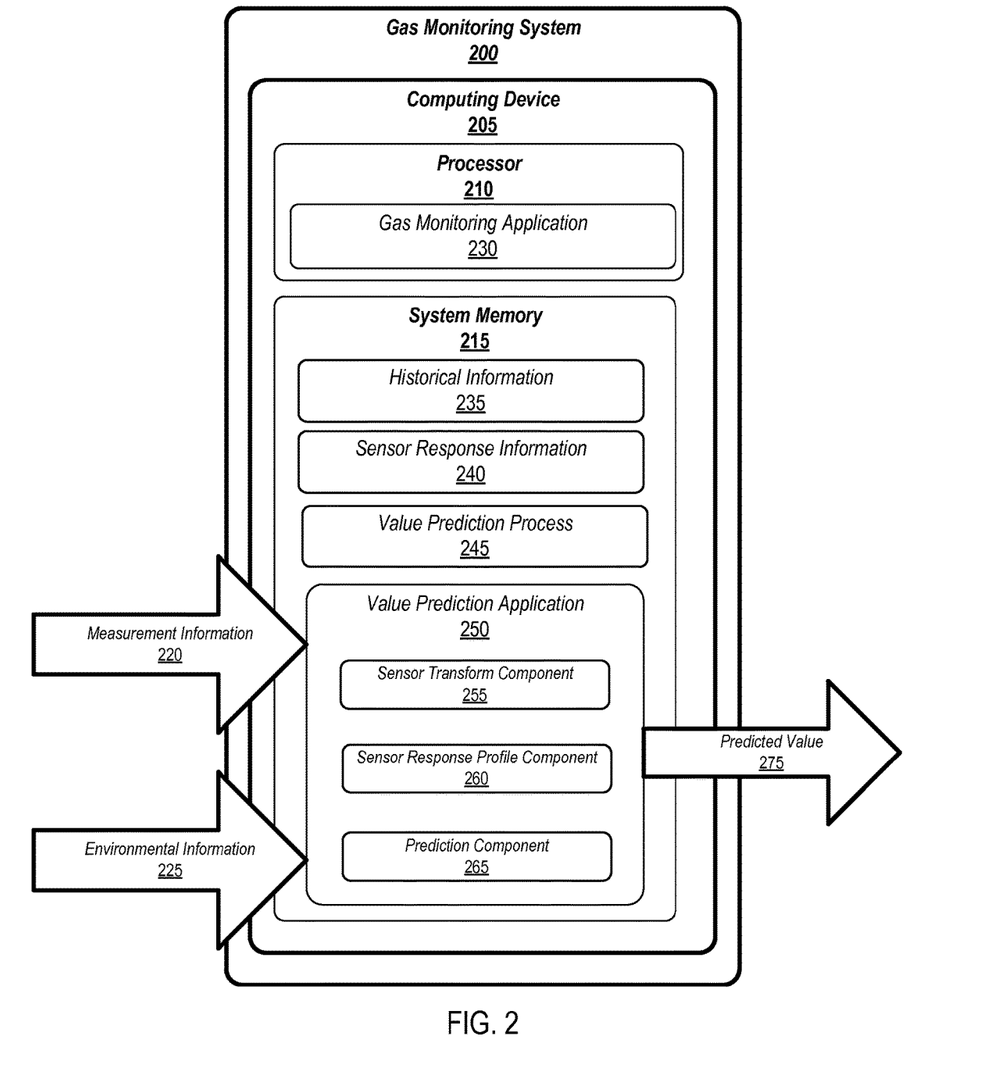
FIG. 2 depicts an illustrative gas monitoring system according to some embodiments.

FIG. 2 depicts an illustrative gas monitoring system according to some embodiments. As shown in FIG. 2, a gas monitoring system 200 may include a computing device 205 having a processor 210 and system memory 215. The computing device 205 may include any type of computing or logic device, such as a gas monitoring device now known to those having ordinary skill in the art or developed in the future. A non-limiting example of a computing device 205 may include a gas monitoring device produced by Industrial Scientific Corporation of Oakdale, Pa., United States (for example, the Tango TX1, the Ventis MX4, or the MX6 iBrid).

The processor 210 may be configured to execute a gas value prediction application (the "value prediction application") 250. The value prediction application 250 may be configured to receive, analyze, and process measurement information 220 from a gas sensor (not shown) operably coupled to the monitoring system 200. In some embodiments, the value prediction application may be configured to, among other things, generate a predicted value 275 based on the measurement information 220.

The value prediction application 250 may include various modules, programs, applications, routines, code, functions, processes, or the like ("components") configured to perform functions according to some embodiments described herein. In some embodiments, the value prediction application 250 may include a sensor transform component 255, a sensor response profile component 265, and a prediction component 265.

In some embodiments, the sensor transform component 255 may be configured to transform gas measurement information 220 into a concentration value (or "concentration information"). For instance, the gas measurement information 220 may include voltage or amperage data and the sensor transform component 255 may convert this data into a concentration, such as ppm, ppb, a volume percentage, a lower explosive limit (LEL) percentage, or the like. In some embodiments, the gas measurement information 220 may include raw gas measurement information. In some embodiments, the sensor transform component 255 may be configured to condition or otherwise process the gas measurement information 220, such as by factoring in sensor ranges, zero output, sensitivity, calibration data, temperature compensation, environmental information 225, or the like. In some embodiments, the environmental information 225 may be obtained by various sensors embedded into or otherwise coupled with the system 200, such as temperature, pressure, light, accelerometer, and air movement sensors. In some embodiments, the environmental information 225 may be used as part of or to develop an environmental profile for a sensor and/or a gas monitoring system 200 based on historical environmental information. For instance, the prediction component 265 may be configured to determine how a gas sensor acted under past environmental conditions in order to determine whether and to what extent current environmental conditions may influence the operation of the gas sensor and/or any measurement information 220 produced thereby.

In some embodiments, the environmental information 225, the gas measurement information 220 and/or the concentration information generated by the sensor transform component 255 may be stored as historical information 235.

The sensor response profile component 260 may be configured to determine, process, or otherwise manage gas sensor response information (or a gas sensor "profile"). The gas sensor response information may be configured to indicate how a gas sensor responds to a detected gas. In some embodiments, the system 200 may include and/or use gas sensors associated with at least one response curve. Each individual gas sensor and/or type of gas sensor may be associated with at least one particular response curve. In some embodiments, the response curve associated with a gas sensor at any time may be determined based on various conditions, such as environmental conditions and/or operational conditions of the system 200. The response curve and any information associated therewith may be stored as sensor response information 240. In some embodiments, the response curve associated with a gas sensor may change over time based on, for instance, calibration information, environmental information 225, measurement information 220, historical information 235, and any predicted values associated with the gas sensor. For instance, the monitoring application 230 may be configured to monitor the accuracy of predicted values generated according to some embodiments and to adjust a response curve to provide more accurate predictions.

Figure 3:
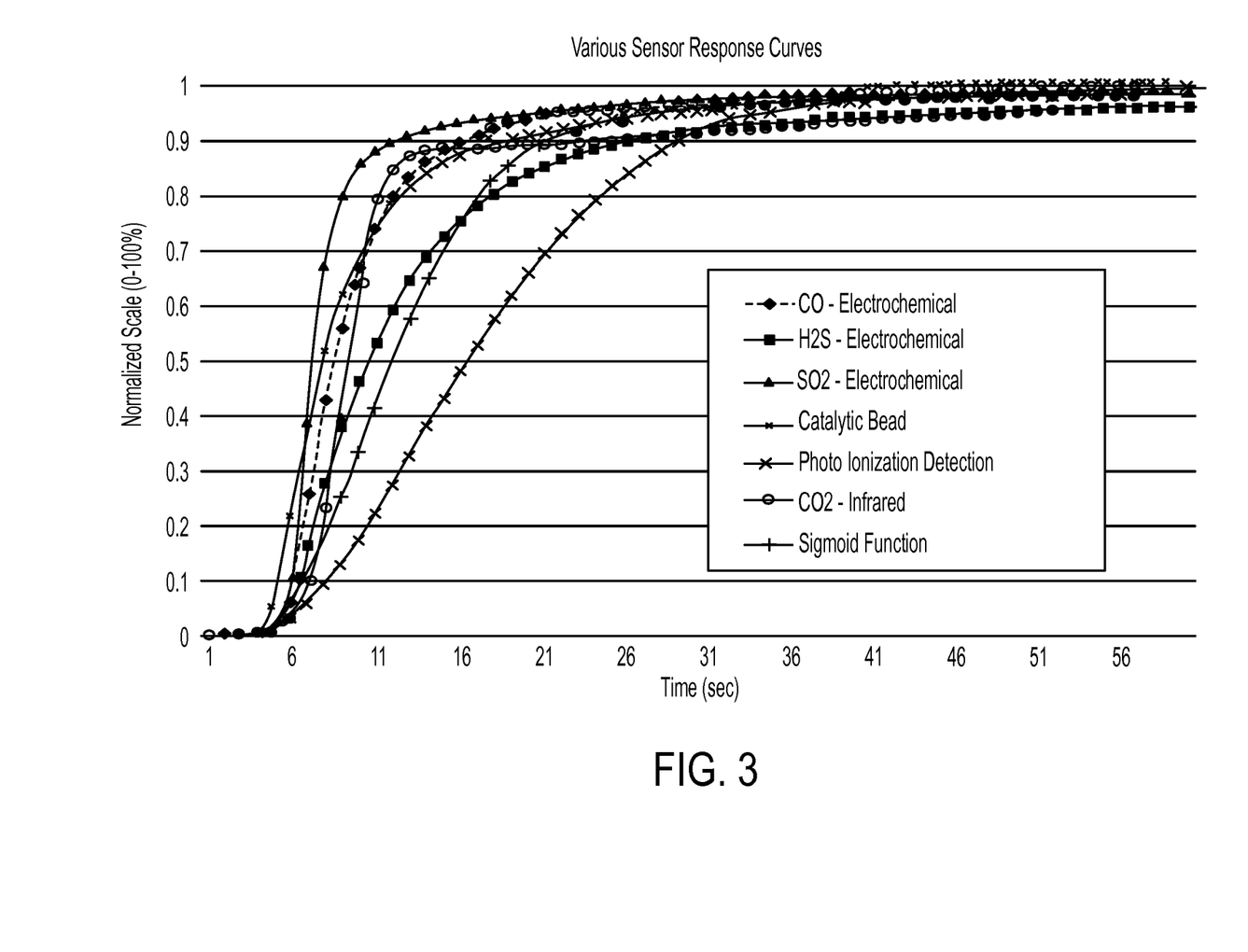
FIG. 3 depicts a typical response curve for a gas sensor according to some embodiments.
Figure 4:
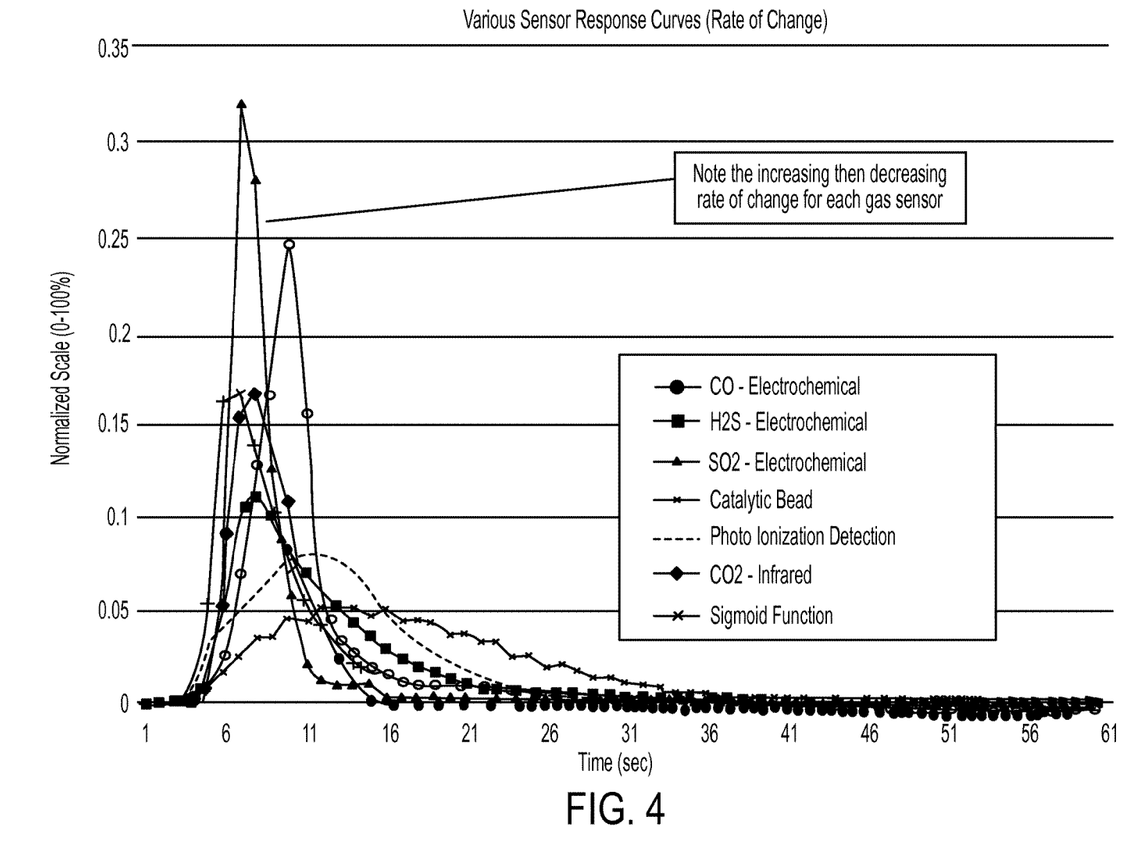
FIG. 4 depicts an illustrative plot of the first derivative of the Sigmoid functions depicted in FIG. 3.

In some embodiments, a response curve may be approximated by various functions, such as a sigmoid function (for instance, a function generally having an "S" shaped curve when expressed on a graph). FIG. 3 depicts a typical response curve for a gas sensor according to some embodiments. In some embodiments, the response curve may be a known repeatable response curve. The Sigmoid function may be generated using various processes or functions, including, without limitation, a logistic curve, a Gompertz curve, an error function, or the like. In some embodiments, the "S" shape of a response curve is achieved because the rate of change of a signal produced by a gas sensor accelerates and then decelerates until reaching a final asymptotic value, which may be visualized by plotting the first derivative of the Sigmoid function "S" shaped curve. FIG. 4 depicts an illustrative plot of the first derivative of the sigmoid functions depicted in FIG. 3. In some embodiments, the deceleration in the sensor output may provide an indication of nearing the asymptotic value. In contrast, for example, if the rate of change of the sensor output was constant, the response curve of the sensor may be a straight sloping line and, as such, there may be no indication of the final asymptotic value until it was reached.

The prediction component 265 may be configured to generate a predicted value 275 based on the measurement information 220, the concentration information, the environmental information 225, the sensor response information 240 and/or the historical information 235. In some embodiments, the system 200 may include a value prediction process 245 which may include programs, algorithms, formulas, processes, applications, functions, or the like for use by the prediction component 265 for generating the predicted value 275. In some embodiments, the sensor response information 240 for a gas sensor may control the rate of change of the sensor output. In some cases, the sensor response information 240 may decrease until reaching zero or substantially reaching zero. In some embodiments, this sensor response information 240 may allow for the approximation of the final asymptotic value based on the historical information 235 associated with the gas sensor, such as the gas sensor output rate of change.

The prediction component 265 may use various processes to generate a predicted value 275. A non-limiting example of a process may include the following:

$$Z_t = Y_t + (Y_{t-1} - Y_{t-2}) + \tfrac{1}{2}(Y_{t-2} - Y_{t-3}) + \tfrac{1}{3}(Y_{t-3} - Y_{t-4}) \quad (1)$$

where $Z_t$=predicted gas measurement at time t, and $Y_t$=raw gas measurement information at time t.

In some embodiments, $Y_t$ may include the concentration information generated by the sensor transform component 255 at time t. In some embodiments, the prediction component 265 may receive the measurement information 220 and may use process (1) to generate the predicted value 275 (for instance, Z).

Most gas sensors do not provide a stable output. For instance, the output may randomly or semi-randomly change about an average "zero" value. Accordingly, in some embodiments, the value prediction application 250 may be configured to prevent such output changes from being interpreted as a gas event. In some embodiments, the value prediction application 250 may use a safeguard process to ensure that only measurement information 220 changes (for instance, gas sensor output changes) due to variations in gas concentration are used by the prediction component 265 to generate a predicted value 275. For example, the value prediction application 250 may filter out and/or prevent the prediction component 265 from generating a predicted value using non-concentration (or "artificial") gas sensor output changes. Non-limiting examples of artificial gas sensor output changes may include temperature, electrical conditions (for example, electromagnetic compatibility (EMC)), noise, or the like. For instance, the monitoring application 250 may be configured to recognize signatures of certain artificial gas sensor output changes. In one example, the monitoring application 250 may be configured to recognize that an erratic negative or positive spike, followed by another erratic spike or a return to zero is consistent with an electromagnetic interference spike and not a gas event. In some embodiments, the prediction component 265 may use a "prediction dead band" that may not allow the prediction component 265 to generate or provide a prediction value 275 if the signal is below a certain threshold. A non-limiting threshold may include 5% of full scale signal.

Most sensors may experience a change in their baseline or "zero value" over time, which is typically a small slow changing value, and/or a sensitivity drop. The prediction component 265 may be configured ton to interpret this change as a gas event and generate a prediction value 275. In some embodiments, the prediction component 265 may use the prediction dead band. In some embodiments, the prediction component 265 may require a certain number of consecutive increasing or decreasing sensor outputs, such as two consecutive increasing or decreasing sensor outputs.

In some embodiments, the value prediction application 250 and, in particular, the prediction component 265, may be configured to operate with substantially any type of gas sensor, including gas sensors having different output scales and for detecting different types of gases. For instance, the value prediction application 250 may be configured to operate with gas sensors having various response times. In some instances, the variation in response times between different sensors may be substantial, varying from a few seconds to as long as sixty seconds. In some embodiments, the prediction component 265 may be configured to operate based on the sign of the rate of change of an output signal. The sign is not linked to the magnitude of the change in sensor output (for instance, response time). The prediction component 265 may be configured to generate a prediction, including each subsequent prediction, based on the magnitude of the sensor output signal change. As such, a small signal change may result in a small prediction and vice versa. In this manner, the prediction component 265 may be uniformly applied to various sensor types and allows for the automatic adaption of the prediction component to sensor performance changes over time.

In some embodiments, the value prediction application 250 may also be configured to operate with gas sensors having various sensitivities through configuration of gas monitor hardware and the sensor transformation component 255. In some embodiments, the value prediction application 250 may be configured to operate with non-zero gas sensors, for instance, oxygen sensors and other gas sensors that do not have an intended steady state reading of zero.

In some embodiments, the value prediction application 250 may be configured to operate with gas sensors having various gas ranges. For instance, the value prediction application 250 may operate substantially the same for a gas sensor having a $NH_3$ detection range of 100 ppm and a gas sensor having a $NH_3$ detection range of 1000 ppm. In some embodiments, the prediction component 265 may be configured to use the actual magnitude of the sensor output change in the sensor information 220 to determine a prediction value 275. As such, a small signal change may result in a small prediction and vice versa.

In some embodiments, the value prediction application 250 may be configured to generate prediction values 275 for decreasing gas sensor output signals and increasing gas output signals, including with substantially similar prediction times. For instance, it would not be beneficial for the value prediction application 250 to provide a T90 time of 10 seconds, but require 40 seconds to return to zero once a target gas has been removed. Accordingly, in some embodiments, the prediction component 265 may base the predicted value 275 on the actual signal change from the last time series (for instance, t−1 to the current time, t). In addition, the prediction component 265 may apply a component of the two previous time series changes (for instance, t−2 and t−3) as shown in process (1), above. In this manner, the predicted value 275 is accurate regardless of whether the concentration of the detected gas is increasing or decreasing. In particular, if the change from the last time series (t−1) is positive, the process (1) may predict a value higher than the current value and vice versa.

A typical use case for the prediction component 265, such as through process (1), may include gas sensors having a steady state reading of zero, followed by a target gas application resulting in a sensor response curve (see FIG. 4) reaching an asymptotic value, followed by a similar return to zero after the target gas has been removed. However, not all gas sensors and conditions may comply with such a typical use case. In a first scenario, a gas sensor may be exposed to a gas concentration that is continually increasing, such as a gas leak within a closed room. In such a scenario, the gas sensor may not reach a final asymptotic value until the room's gas concentration had stabilized. Nonetheless, the prediction component 265 may be configured to provide reliable and accurate predicted values 275 because the predicted value may be based on the actual sensor output change experienced in a subsequent time series. As such, as the room's gas concentration steadily increases, the predicted value 275 may also increase until the room's gas concentration stabilizes, at which point, the sensor output rate of change may begin to decrease, resulting in an equivalent decrease in the predicted value.

In a second scenario, the prediction component 265 may be configured to provide reliable and accurate predicted values 275 for a gas sensor exposed to a 100% or substantially 100% nitrogen environment, for example, in an effort to clear the sensor of a residual target gas and to achieve a zero reading more quickly.

Figure 5:
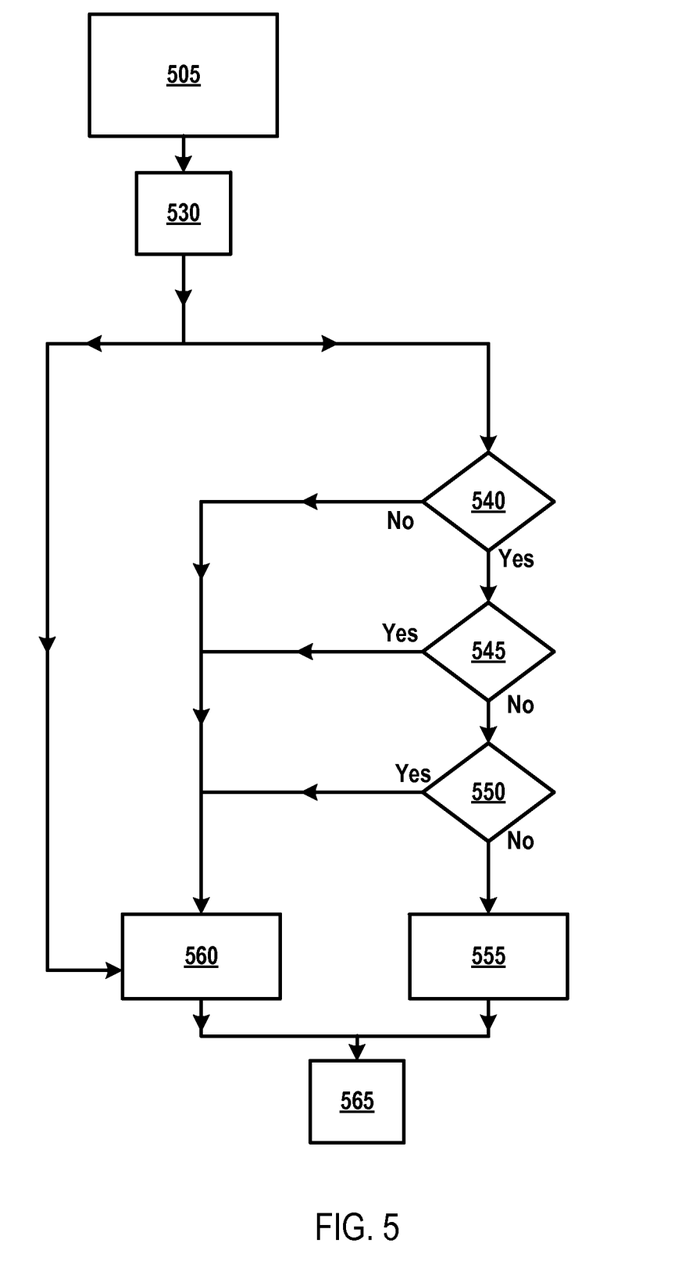
FIG. 5 depicts a flow diagram for an illustrative method of generating a prediction value according to some embodiments.

FIG. 5 depicts a flow diagram for an illustrative method of generating a prediction value according to some embodiments. The method depicted in FIG. 5 may be carried out using systems configured according to some embodiments, such as system 100 of FIG. 1 or system 200 of FIG. 2. As shown in FIG. 5, a monitoring system may receive 505 gas measurement information, such as $X_t$ of process (1). In some embodiments, the gas measurement information may be received 505 by a transform function configured to transform 530 the gas measurement information into a concentration value, such as $Y_t$ of process (1). In some embodiments, the transform function may be configured in a manner that is the same as or similar to the sensor transform component 255 described above in reference to FIG. 2. In some embodiments, the transform function may receive various sensor transform parameters configured to specify the transform process for the particular gas measurement information and/or concentration value. In addition, the transform function may receive environmental information stored, for instance, in a system memory. The concentration value may be stored, for example, as historical information 235 in a system memory 215 as depicted in FIG. 2.

The system may determine 540 whether a valid exposure profile has been established to ensure that the signal trend is consistent with gas exposure and not artificial conditions. For instance, the system may determine 540 whether the change in concentration 530 (for instance, $Y_t$) has increased or decreased in two consecutive time series. If it is determined 540 that there is not a valid exposure profile, the system may condition 560 the concentration value 530 as present 565 as an output value. The concentration value 530 may be conditioned 560 using various processes, such as a conventional steady state smoothing algorithm for filtering noise and smoothing the output signal. In some embodiments, the steady state smoothing algorithm may include an average of several concentration readings.

Gas sensors may experience a change in output when exposed to external environmental changes (or "environmental transients"), such as temperature, humidity, or pressure. Accordingly, if it is determined 540 that there is a valid exposure profile, the system may determine 545 whether there has been such an environmental transient using, among other things, the environmental information 525, including historical environmental information. This determination 545 may be configured to avoid use of the prediction process to generate a predicted value during states of environmental transients. In some embodiments, if it is determined 545 that there are environmental transients, the system may characterize the response curve of a gas sensor as being due to environmental change and then restrict the generation of prediction values when such a condition is reached.

In some embodiments, if it is determined 545 that no environmental transients are present, then it may be determined 550 whether the signal change is due to signal noise. For instance, the system may determine 550 that a signal change is due to noise if a signal change is greater than zero and less than or equal to a dead band value. If it is determined 350 that the signal change is not due to signal noise, then the system may generate 555 a predicted value according to some embodiments and present 565 the predicted value as an output value.

Figure 6:
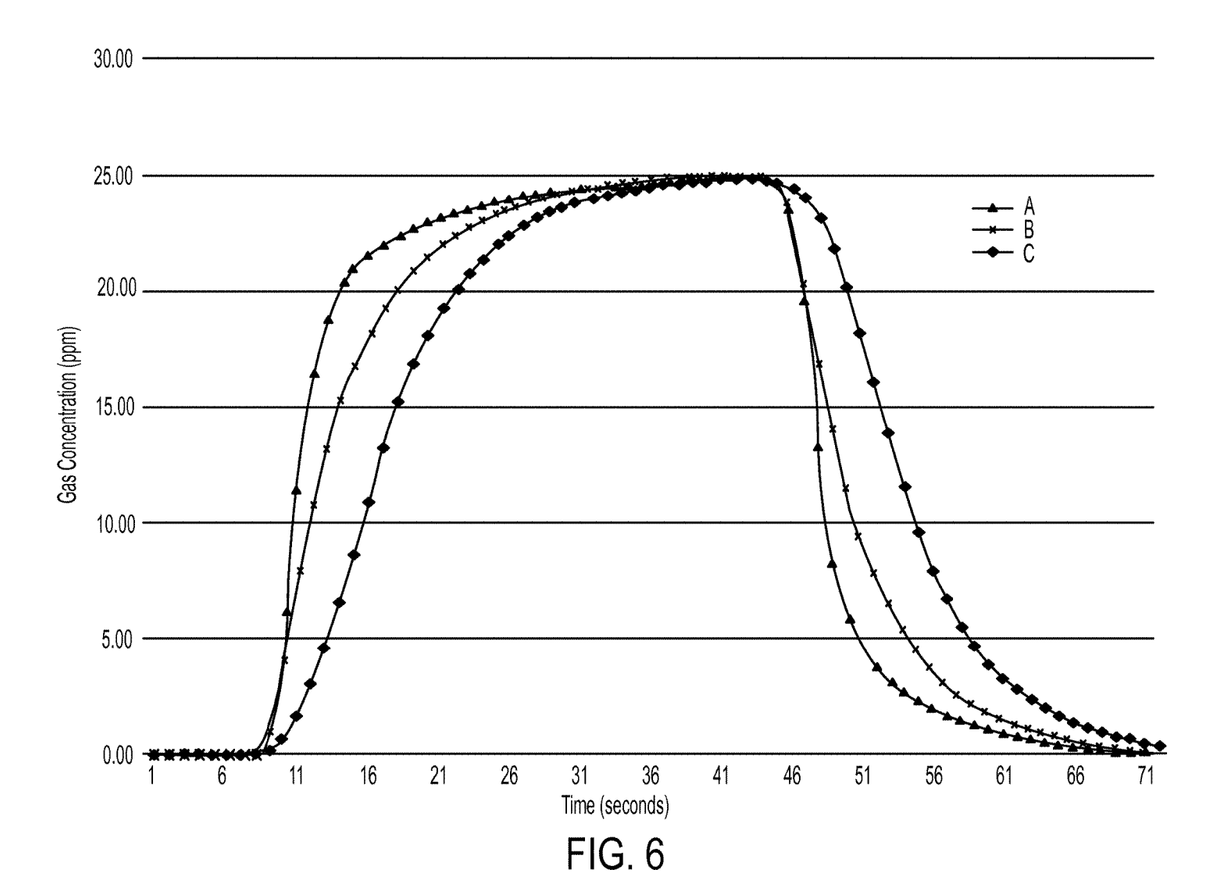
FIG. 6 depicts a graph of response time curves for a prediction process configured according to some embodiments, a raw sensor output, and a conventional signal smoothing process.

FIG. 6 depicts a graph of response time curve A for a prediction process configured according to some embodiments, a response time curve B for raw sensor output, and a response time curve C for a conventional signal smoothing process. As shown in FIG. 6, use of a prediction process configured according to some embodiments generates the surprising result of a response time curve A as compared with the response time curves B and C. Therefore, a gas monitoring system configured according to some embodiments may have an improved speed or response time compared with conventional gas monitoring devices.

FIG. 7 depicts a block diagram of exemplary internal hardware that may be used to contain or implement the various computer processes and systems as discussed above. A bus 700 serves as the main information highway interconnecting the other illustrated components of the hardware. CPU 705 is the central processing unit of the system, performing calculations and logic operations required to execute a program. CPU 705 is an exemplary processing device, computing device or processor as such terms are used within this disclosure. Read only memory (ROM) 730 and random access memory (RAM) 735 constitute exemplary memory devices.

A controller 720 interfaces with one or more optional memory devices 725 via the system bus 700. These memory devices 725 may include, for example, an external or internal DVD drive, a CD ROM drive, a hard drive, flash memory, a USB drive or the like. As indicated previously, these various drives and controllers are optional devices. Additionally, the memory devices 725 may be configured to include individual files for storing any software modules or instructions, auxiliary data, common files for storing groups of results or auxiliary, or one or more databases for storing the result information, auxiliary data, and related information as discussed above.

Program instructions, software or interactive modules for performing any of the functional steps associated with the determination, configuration, transmission, decoding, or the like of the presentation settings as described above may be stored in the ROM 730 and/or the RAM 735. Optionally, the program instructions may be stored on a tangible computer-readable medium such as a compact disk, a digital disk, flash memory, a memory card, a USB drive, an optical disc storage medium, such as a Blu-ray™ disc, and/or other recording medium.

An optional display interface 730 can permit information from the bus 700 to be displayed on the display 735 in audio, visual, graphic or alphanumeric format. The information may include information related to a current job ticket and associated tasks. Communication with external devices may occur using various communication ports 770. An exemplary communication port 7700 may be attached to a communications network, such as the Internet or a local area network.

The hardware may also include an interface 775 which allows for receipt of data from input devices such as a keyboard 750 or other input device 755 such as a mouse, a joystick, a touch screen, a remote control, a pointing device, a video input device and/or an audio input device.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A gas monitoring system, comprising:
a gas sensor;
a processor; and
a non-transitory, computer-readable storage medium in operable communication with the processor, wherein the computer-readable storage medium contains one or more programming instructions that, when executed, cause the processor to:
receive gas measurement information in a time series from the gas sensor for a concentration of a gas,
store the gas measurement information as historical gas measurement information,
receive a gas sensor response sigmoid function having a specific shape and corresponding to the gas sensor,
determine a rate of change of the concentration of the gas at each of a plurality of times using the gas measurement information,
generate a predicted gas measurement value for the gas sensor corresponding to the concentration of gas by predicting an asymptotic value of the gas measurement information using the gas measurement information corresponding to a specific time and a set of weighted determined rates of change prior to the specific time, wherein each corresponding weight for the set of weighted determined rates of change uses the specific shape of the gas sensor response sigmoid function, and
trigger an alarm when the predicted gas measurement value is outside a desired range,
wherein the computer-readable storage medium further contains one or more programming instructions that, when executed, cause the processor to:
receive environmental information,
determine whether a change in the gas measurement information occurs responsive to the environmental information and not a change in the concentration of the gas, and
prevent the generation of the predicted gas measurement value using the change in the gas measurement information occurring responsive to the environmental information.

2. The system of claim 1, wherein the gas comprises carbon monoxide (CO), oxygen ($O_2$), hydrogen sulfide ($H_2S$), nitrogen dioxide ($NO_2$), and/or sulfur dioxide ($SO_2$).

3. The system of claim 1, wherein the computer-readable storage medium further contains one or more programming instructions that, when executed, cause the processor to update the gas sensor response sigmoid function using the historical gas measurement information.

4. The system of claim 1, wherein the computer-readable storage medium further contains one or more programming instructions that, when executed, cause the processor to determine whether a change in the gas measurement information occurs responsive to an artificial factor or responsive to a gas event.

5. The system of claim 1, wherein the computer-readable storage medium further contains one or more programming instructions that, when executed, cause the processor to prevent the generation of the predicted gas measurement value using an artificial factor.

6. The system of claim 1, wherein the gas sensor comprises at least one of a semiconductor sensor, an electrochemical sensor, a catalytic sensor, and a photoionization sensor.

7. The system of claim 1, wherein the generation of the predicted gas measurement value comprises the following process:

$$Z_t = Y_t + (Y_{t-1} - Y_{t-2}) + \tfrac{1}{2}(Y_{t-2} - Y_{t-3}) + \tfrac{1}{3}(Y_{t-3} - Y_{t-4})$$

where $Z_1$=predicted value at time t, and
$Y_1$=raw gas measurement information at time t.

8. A computer-implemented method for monitoring a gas, the method comprising, by a processor:
receiving gas measurement information from a gas sensor in a time series for a concentration of a gas;

storing the gas measurement information as historical gas measurement information;
receiving a gas sensor response sigmoid function having a specific shape and corresponding to the gas sensor;
determining a rate of change of the concentration of the gas using the gas measurement information at each of a plurality of times;
receiving environmental information;
determining whether a change in the gas measurement information occurs responsive to the environmental information and not a change in the concentration of the gas;
generating a predicted gas measurement value for the gas sensor corresponding to the concentration of gas by predicting an asymptotic value of the gas measurement information using the gas measurement information corresponding to a specific time and a set of weighted determined rates of change prior to the specific time, wherein each corresponding weight for the set of weighted determined rates of change uses the specific shape of the gas sensor response sigmoid function;
preventing the generation of the predicted gas measurement value using the change in the gas measurement information occurring responsive to the environmental information; and
generating an alarm trigger when the predicted gas measurement value is outside of a predetermined range.

9. The method of claim 8, wherein the gas comprises carbon monoxide (CO), oxygen ($O_2$), hydrogen sulfide ($H_2S$), nitrogen dioxide ($NO_2$), and/or sulfur dioxide ($SO_2$).

10. The method of claim 8, further comprising updating the gas sensor response sigmoid function using the historical gas measurement information.

11. The method of claim 8, further comprising determining whether a change in the gas measurement information occurs responsive to an artificial factor or responsive to a gas event.

12. The method of claim 8, further comprising preventing the generation of the predicted gas measurement value using an artificial factor.

13. The method of claim 8, wherein the gas sensor comprises at least one of a semiconductor sensor, an electrochemical sensor, a catalytic sensor, and a photoionization sensor.

14. The method of claim 8, wherein the generation of the predicted gas measurement value comprises the following process:

$$Zt = Y_t + (Y_{t-1} - Y_{t-2}) + \frac{1}{2}(Y_{t-2} - Y_{t-3}) + \frac{1}{3}(Y_{t-3} - Y_{t-4})$$

where $Z_1$=predicted value at time t, and
$Y_1$=raw gas measurement information at time t.

* * * * *

UNITED STATES PATENT AND TRADEMARK OFFICE
CERTIFICATE OF CORRECTION

PATENT NO. : 10,466,221 B2
APPLICATION NO. : 15/106452
DATED : November 5, 2019
INVENTOR(S) : Christopher Todd Yocum Page 1 of 1

It is certified that error appears in the above-identified patent and that said Letters Patent is hereby corrected as shown below:

In the Specification

In Column 8, Line 15, delete "Z)." and insert -- $Z_t$). --, therefor.

In Column 13, Line 39, after "cetera" insert -- . --.

In Column 13, Line 41, after "cetera" insert -- . --.

Signed and Sealed this
Eleventh Day of February, 2020

Andrei Iancu
*Director of the United States Patent and Trademark Office*